US007939312B2

(12) United States Patent
Roberts et al.

(10) Patent No.: US 7,939,312 B2
(45) Date of Patent: May 10, 2011

(54) RAPID THERMOCYCLER WITH MOVABLE COOLING ASSEMBLY

(75) Inventors: Danvern R. Roberts, Las Vegas, NV (US); William D. Bickmore, Jr., St. George, UT (US); Jared S. Hummel, St. George, UT (US)

(73) Assignee: DxNA LLC, St. George, UT (US)

( * ) Notice: Subject to any disclaimer, the term of this patent is extended or adjusted under 35 U.S.C. 154(b) by 696 days.

(21) Appl. No.: 11/697,917

(22) Filed: Apr. 9, 2007

(65) Prior Publication Data

US 2008/0057542 A1 Mar. 6, 2008

Related U.S. Application Data

(60) Provisional application No. 60/824,027, filed on Aug. 30, 2006.

(51) Int. Cl.
*C12M 1/38* (2006.01)

(52) U.S. Cl. .................................. 435/286.1; 435/287.2

(58) Field of Classification Search ................. 435/91.2, 435/286.1, 287.2

See application file for complete search history.

(56) References Cited

U.S. PATENT DOCUMENTS 4,686,606 A * 8/1987 Yamada et al. ............... 361/699
5,985,651 A * 11/1999 Hunicke-Smith .......... 435/285.1
6,180,372 B1 * 1/2001 Franzen ....................... 435/91.1
6,558,947 B1 * 5/2003 Lund et al. ................. 435/303.1
6,814,934 B1 * 11/2004 Higuchi ..................... 422/82.08
6,875,619 B2 * 4/2005 Blackburn ......................... 506/9
2004/0043479 A1 * 3/2004 Briscoe et al. ............. 435/288.5
2008/0050781 A1 * 2/2008 Oldham et al. .............. 435/91.2
2008/0248586 A1 * 10/2008 Tajima .......................... 436/164
2008/0254517 A1 * 10/2008 Mortillaro et al. ........... 435/91.2

FOREIGN PATENT DOCUMENTS

CA 1125967 * 6/1982
JP 2005-117987 * 5/2005

OTHER PUBLICATIONS

International Search Report for PCT/US2007/18946, mailed Sep. 17, 2008.
Written Opinion of the International Searching Authority for PCT/US2007/18946, mailed Sep. 17, 2008.

* cited by examiner

*Primary Examiner* — Kenneth R. Horlick
(74) *Attorney, Agent, or Firm* — Holme Roberts & Owen LLP

(57) ABSTRACT

Methods and apparatus for effecting rapid thermocycling in connection with the polymerase chain reaction are disclosed. A sample assembly having a relatively small thermal mass is heated to desired PCR operating temperatures, and a separate cooling assembly is used to rapidly lower the temperature as required. In one embodiment, a sample assembly with an integrated heating element is isolated from a relatively large thermal mass cold sink when the temperature of a sample is to be raised or maintained, and brought in contact with the cold sink when the temperature is desired to be lowered.

16 Claims, 5 Drawing Sheets

RAPID THERMOCYCLER WITH MOVABLE COOLING ASSEMBLY

CROSS-REFERENCE TO RELATED APPLICATIONS

This application claims priority to Provisional Application No. 60/824,027, entitled "Rapid Thermal Cycler" and filed on Aug. 30, 2006, which is incorporated herein by reference.

BACKGROUND OF THE INVENTION

1. The Field of the Invention

The present invention is directed to the field of thermocyclers used in the practice of the polymerase chain reaction (PCR).

2. The Relevant Technology

A number of industrial, technology and research applications utilize thermal cycling to manage applications such as chemical or biochemical reactions or analytical applications.

One important tool in the field of molecular biology which utilizes thermal cycling is the process known as "polymerase chain reaction" (PCR). PCR generates large quantities of genetic material from small samples of the genetic material. This is important because small samples of genetic material may be difficult or expensive to measure or analyze or use for any practical purpose, whereas the ability to produce large amounts of desired genetic material through the PCR amplification process allows one to engage in important actions such as the identification of particular genetic material in a sample, or the measurement of how much genetic material was present, or generation of enough genetic material for use to serve as a component of further applications.

The PCR process is performed in a small reaction vial containing components for DNA duplication: the DNA to be duplicated, the four nucleotides which are assembled to form DNA, two different types of synthetic DNA called "primers" (one for each of the complementary strands of DNA), and an enzyme called DNA polymerase.

DNA is double stranded. The PCR process begins by separating the two strands of DNA into individual complementary strands, a step which is referred to as "denaturation." This is typically accomplished by heating the PCR reaction mixture to a temperature of about 94 to 96 degrees centigrade for a period of time between a few seconds to over a minute in duration.

Once the DNA is separated into single strands, the mixture is cooled to about 45 to about 60 degrees centigrade (typically chosen to be about 5 degrees below the primer melting temperature) in order to allow a primer to bind to each of the corresponding single strands of DNA in the mixture. This step is typically called "annealing." The annealing step typically takes anywhere from a few seconds up to a few minutes.

Next, the reaction vessel is heated to about 72 to 73 degrees centigrade, a temperature at which DNA polymerase in the reaction mixture acts to build a second strand of DNA onto the single strand by adding nucleic acids onto the primer so as to form a double stranded DNA that is identical to that of the original strand of DNA. This step is generally called "extension." The extension step generally takes from a few seconds to a couple minutes to complete.

This series of three steps, also sometimes referred to as "stages", define one "cycle." Completion of a PCR cycle results in doubling the amount of DNA in the reaction vial. Repeating a cycle results in another doubling of the amount of DNA in the reaction vial. Typically, the process is repeated many times, e.g. 10 to 40 times, resulting in a large number of identical pieces of DNA. Performing 20 cycles results in more than a million copies of the original DNA sample. Performing 30 cycles results in more than a billion copies of the original DNA sample. A "thermocycler" is used to automate the process of moving the reaction vessel between the desired temperatures for the desired period of time.

It can take about three hours to run about 30 cycles when using conventional equipment. This amount of time is required because of the time that is spent accomplishing a change of temperature between each PCR step, as well as the time required at each target temperature.

BRIEF SUMMARY OF THE INVENTION

Although the ability to make over a million copies in a few hours was a tremendously important advance in the field of molecular biology, it would be of great value to be able to decrease the time required to run each PCR cycle.

The present invention provides methods and apparatus that permit for more rapid operation of the polymerase chain reaction by decreasing the amount of time required at each step. This is accomplished by utilizing a sample assembly having a relatively small thermal mass and an associated heating element that is capable of rapidly heating the sample assembly to a desired temperature and then maintaining it at that temperature. A separate cooling assembly including a cold sink having a relatively large thermal mass is used to rapidly lower the temperature of the sample assembly as required by bringing the cold sink into physical contact with the sample assembly.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The polymerase chain reaction is an important tool for use as a precursor for a number of activities, such as the identification of small amounts of a particular genetic material in a sample, measurement of how much genetic material is present in a sample, or generation of enough genetic material for use in various applications. The present invention provides improvements in thermocyclers used in connection with the polymerase chain reaction.

Conventional thermocyclers have taken a number of forms. Perhaps the most common structure incorporates a large, solid, thermally conductive block having wells formed therein that are adapted to receive small reaction vials. In the context of a thermocycler for use in the performance of PCR, a conventional block contains a number of conical-like wells, typically 96 wells, that accept reaction vials of a corresponding size and shape. A large metal block is used to provide a large thermal mass that is intended to bring all of the reaction vials to the correct reaction temperature quickly and simultaneously, and to hold them at the same temperature throughout the intended reaction duration. This is important so that one can insure that every vial proceed to a similar degree along the reaction path during the course of a cycle of the thermocycler. Failure to maintain all of the reaction vials at the appropriate temperature can, for example, result in a failure in one or more vials to properly denature, anneal or extend the contents of affected vials.

The use of sample blocks having a large thermal mass requires a significant amount of time to raise or lower the temperature of the block to a target temperature for successive steps of each PCR cycle. In contrast to thermocyclers which utilize a high thermal mass block, the present invention provides a different approach, which allows for rapid temperature changes between the various stages of a thermocycler cycle. The present invention reduces the amount of time required for each PCR cycle and reduces the amount of time that a reaction vial is near, but not at, each target temperature.

Figure 1A:
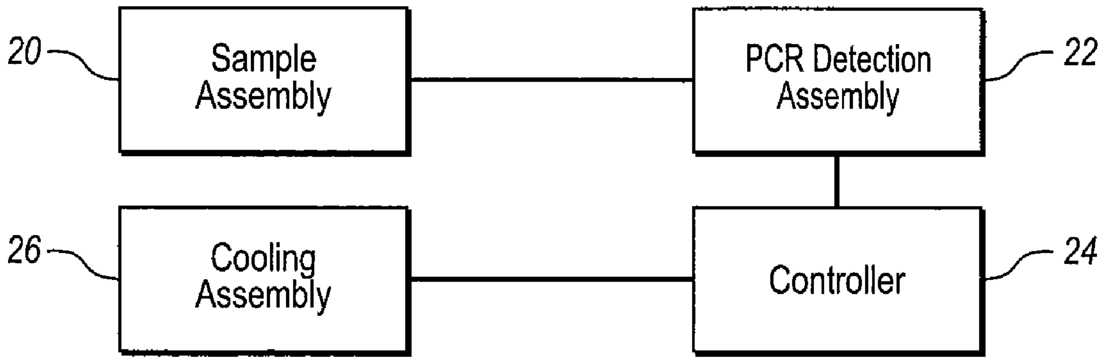
FIG. 1A is a diagrammatic representation of various components of a rapid thermocycler in one configuration in which a sample is thermally isolated.
Figure 1B:
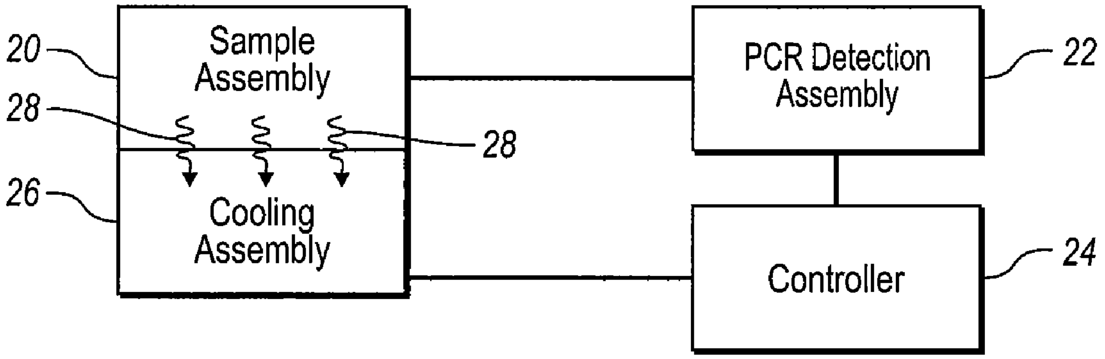
FIG. 1B is a diagrammatic representation similar to FIG. 1B, but showing a different configuration which results cooling of the sample.

FIGS. 1A and 1B illustrate schematically some components of a rapid thermocycler in accordance with one aspect of the invention. Specifically, FIG. 1A depicts a sample assembly 20, which is configured to receive one or more samples containing DNA or cDNA sought to be amplified, and which includes or is associated with a heating element capable of raising the temperature of the samples to a desired temperature, and of maintaining the samples at that temperature.

Sample assembly 20 is optionally associated with a PCR detection system 22, which monitors the status of the polymerase chain reaction on a real time basis as it proceeds within the sample assembly, or observes if it fails to proceed.

Sample assembly 20 is also associated with a controller 24, which controls the temperature of the sample assembly during the various steps of a PCR cycle. Controller 24 is also associated with a cooling assembly 26.

In FIG. 1A, sample assembly 20 is depicted as being thermally isolated from cooling assembly 26 by physical separation between the sample assembly and the cooling assembly. FIG. 1B shows the same components as FIG. 1A, but depicts sample assembly 20 in physical contact with cooling assembly 26, causing heat to be transferred from the sample assembly to the cooling assembly as indicated by arrows 28.

Samples containing DNA to be amplified and the necessary PCR chemical constituents are placed into sample assembly 20. As noted, sample assembly 20 includes a heating element capable of raising the temperature to the various target temperatures of the PCR cycle, and of maintaining such temperatures once they are attained. Controller 24 monitors and controls the temperature of the sample assembly, and preferably also controls the duration of each step of the PCR process. Controller 24 also controls separation of the cooling assembly from the sample assembly during a PCR step, and brings the sample assembly and cooling assembly into physical contact when it is desired to lower the temperature of the sample assembly. This can be accomplished by holding either the sample assembly or the cooling assembly stationary and moving the other from a position separated from or in contact with the other, or both can be moved. Preferably, however, the sample assembly is held immobile so that a PCR detection system, which may include optics involving delicate alignments, is not subject to possible adverse effects caused by movement.

Sample assembly 20 can be designed to hold a single sample, but more commonly will hold multiple samples. For small portable thermocyclers, it is likely that a small number of disposable sample vials will be accommodated by the sample assembly in order to allow for a small form factor and low energy requirements, but, the thermocycler of the present invention can be scaled up so as to accommodate many samples either by scaling up the size of respective sample and cooling assemblies or by providing multiple sample assemblies and multiple cooling assemblies.

Sample assembly 20 will preferably have a relatively small thermal mass so as to be capable of relatively rapid increase or reduction in temperature during the course of a PCR cycle, but it will be appreciated that the actual thermal mass can vary in view of the particular PCR requirements, the materials of the sample assembly, and other components such as the heating element and cooling assembly being used. For rapid thermocycling, it is presently preferred that the combination of the sample assembly, heating element and cooling assembly is such that the sample holder is capable of temperature increase or decrease of at least 5 degrees C. per second, although it will be appreciated that when rapid PCR is not a requirement, the design utilizing a sample assembly associated with or incorporating a heating element and with a movable cold sink would still be an engineering improvement over the use of conventional sample blocks having a large thermal mass.

Sample assembly 20 can contain a resistive heating element, a ceramic type heating element, a solid state device such as a metallic oxide field effect transistor (MOSFET), or other component having a controllable heat output. The heating element may be pulse width modulated or voltage modulated or otherwise controlled so as to raise and maintain the sample assembly at a desired temperature. As noted, it is preferred that the choice of a heating element permit rapid heating of the sample assembly at a rate of at least 5 degrees C. per second. It is also preferred that the heating element be capable of operation without significant overheating of the sample assembly during the PCR cycle. This is best effected if its heat output may be quickly adjusted.

PCR detection system 22 is used to monitor the state of each PCR step. PCR detection system 22 can embrace any approach that allows monitoring of the PCR steps, but it is currently preferred that an optical system be used, and even more preferred that a fluorescent optical system be used. US Publication No. US 2006/0152727 A1, incorporated herein by reference, describes an optical system useful for measurement of small amounts of fluorescence in PCR samples. The use of a PCR detection system is optional, although its use is greatly preferred for efficient PCR.

Controller 24 may take various forms, ranging from a simple mechanical controller that runs each PCR step for a set time at set temperatures, to a more sophisticated controller that would allow customization or would operate in conjunction with a PCR monitoring system to optimize every PCR step by monitoring in real time when each step is completed.

Controller 24 may, by way of non-limiting examples, monitor and control the temperatures, control the cycle times, control the timing and movement of the respective positions of the sample assembly and/or cooling assembly between positions in contact with one another and physically isolated from one another, control operation of the heating element in the sample assembly, record electronic readings from the optical system to memory and to peripheral equipment such as chart recorders and printers, interface with a user, and provide digital information to an external connection or memory. It is preferred that controller 24 take the form of a computer, wherein the term "computer" as used herein is used broadly to include use of a programmable logic controller or other structure capable of performing this function.

Cooling assembly 26 is held at a temperature at or below the lowest temperature at which the sample assembly will operate. It is preferred that the cooling assembly be at a temperature substantially lower than such a lowest temperature and that cooling assembly 26 have a thermal mass substantially higher than the thermal mass of sample assembly 20 in order to more rapidly cool the sample assembly when the cooling assembly and the sample assembly are brought into contact. It will be appreciated that although monitoring of the sample assembly can allow changes in the temperature of the cooling assembly to change during use, it is preferred that the cooling assembly be actively cooled so as to maintain it at a relatively constant temperature so that its cooling capabilities are relatively constant throughout a PCR regimen.

Figure 2:
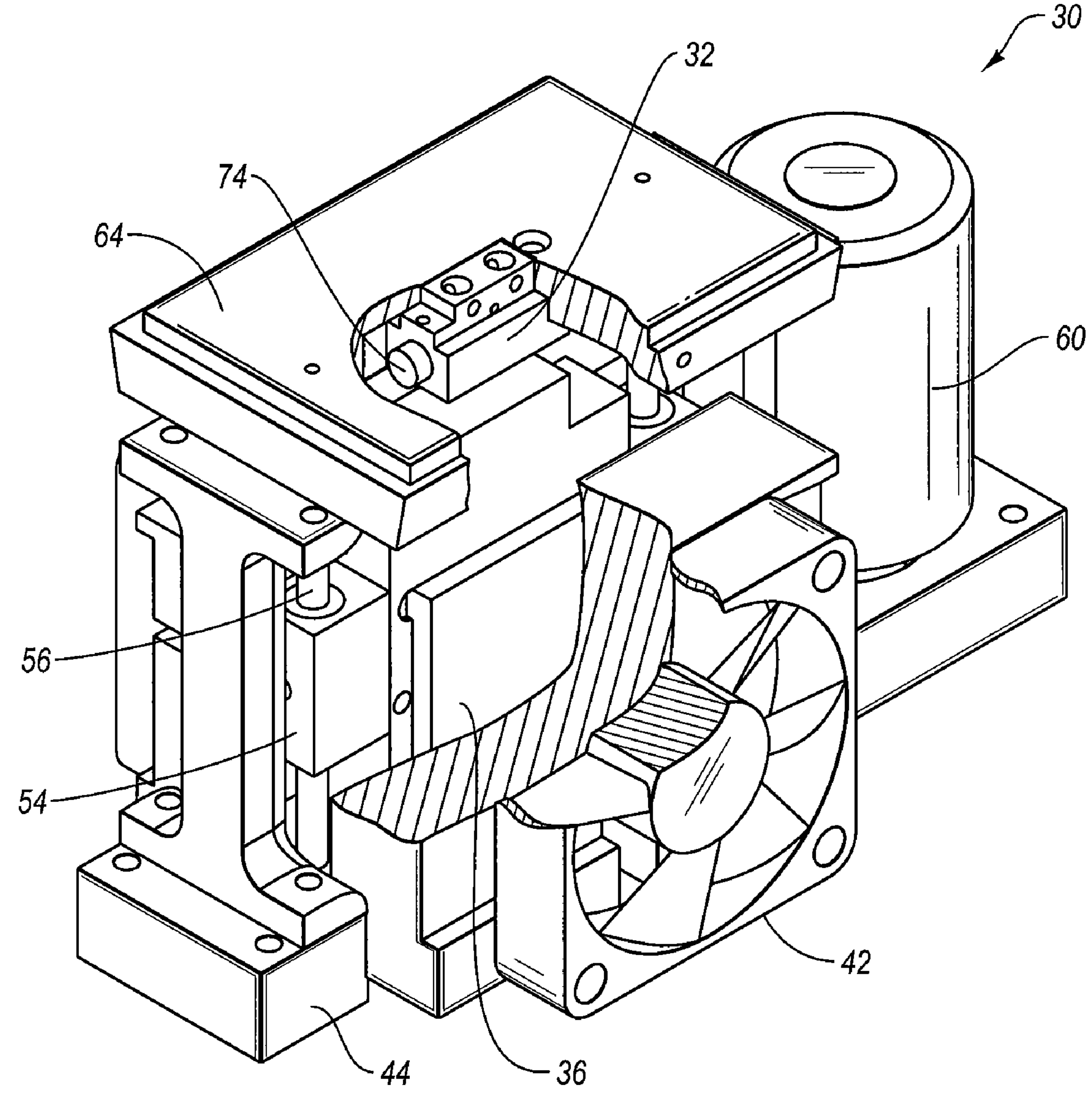
FIG. 2 is a perspective view of an illustrative embodiment of a rapid thermocycler.

FIG. 2 is a perspective view of an illustrative embodiment of a thermocycler 30. FIG. 2 illustrates the use of one embodiment of a sample module 32 which serves the role of a sample assembly of FIG. 1. A cold sink 34, shown in FIG. 1 as being mechanically isolated from sample module 32, serves as a component of a cooling assembly. Although not shown in FIG. 2, a controller is provided to control the functions discussed below. Although a PCR detection assembly is also omitted from FIG. 2, it is preferred that one be provided for reasons already noted.

Figure 3:
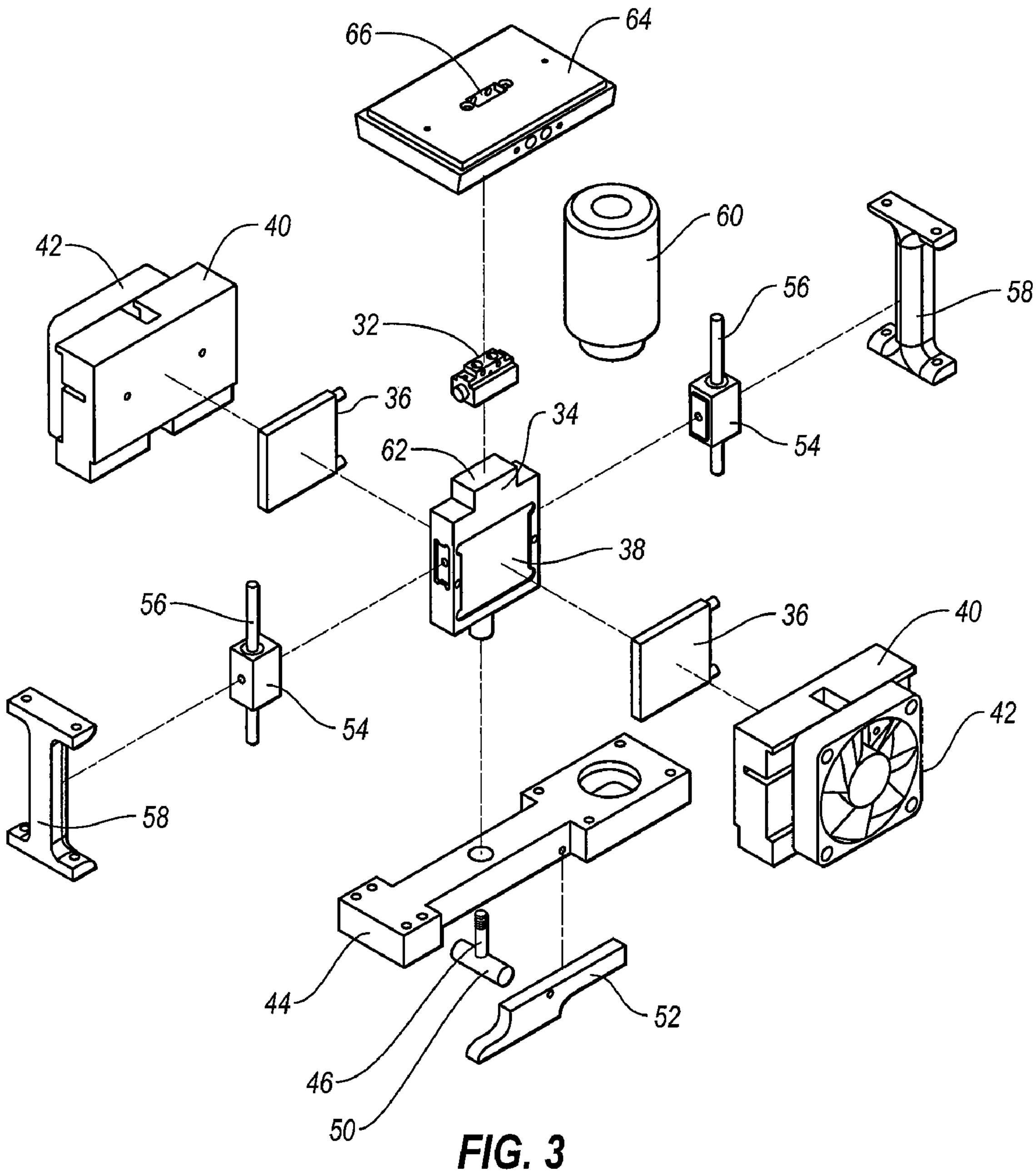
FIG. 3 is an exploded view of various components of the embodiment of FIG. 2.

Some of the components of FIG. 2 are more easily understood by reference to FIG. 3 in juxtaposition with FIG. 2. FIG. 3 is an exploded view of FIG. 2, and depicts cold sink 34 as being at the heart of a cooling assembly. Cold sink 34 is preferably a solid block of material which makes up a relatively large thermal mass in comparison to the thermal mass of the sample module. Cold sink 34 may be fabricated from any material that has a high heat transfer rate, and preferably also has a high heat storage capacity. One suitable material for the cold sink is copper. More than one cold sink may be used.

Conventional thermoelectric coolers 36 (TECs) are advantageously provided on opposite sides of cold sink 34. FIGS. 2 and 3 show thermoelectric coolers 36 as fitting into recesses 38 formed on opposite sides of the cold sink, which assist in placement of the TECs as well as assisting to insure the TECs are in intimate contact with the cold sink. The "cold" side of the TECs are attached to cold sink 34, and the "hot" side of the TECs face outwardly.

The efficiency of the TECs is improved by rapid removal of heat from the "hot" side of the TECs. This may be accomplished by placing active heat sinks 40 in intimate contact with the "hot" side of the thermoelectric coolers in order to draw heat from the TECs. Fans on the outside of heat sinks 40 operate to remove heat from the heat sinks and away from thermocycler 30. The attachment surfaces of the TECs are preferably coated with any one of a variety of heat transfer greases, fluids, or tapes to facilitate a more rapid transfer of heat from cold sink 34 to the TECs, and from the TECs to active heat sinks 40.

Although various approaches may be used to effect isolation or contact of the cold sink with the sample module, the illustrated embodiment shows cold sink 34 as being movably mounted to a base plate 44 by means of a rod 46 which passes slidably through an orifice 48 in the base plate and is fixed to the underside of the cold sink. Rod 46 is advantageously provided with a T-shaped bottom end which rests on a lever arm 52, which in turn is pivotally connected to base plate 44. The weight of the cooling assembly biases the lever arm downwardly, causing the cold sink to assume a spaced apart relationship to the sample module.

Cold sink 34 is also mounted on each side to bearing assemblies 54, which slidably accept respective guide rods 56. Bearing assemblies 54 are secured to respective support brackets 58 which are affixed to base plate 44. The combination of support brackets 58, guide rods 56 and bearing assemblies 54 allow movement of the cold sink between a raised position in contact with the sample module and a lowered position that is spaced from the sample module.

Figure 4A:
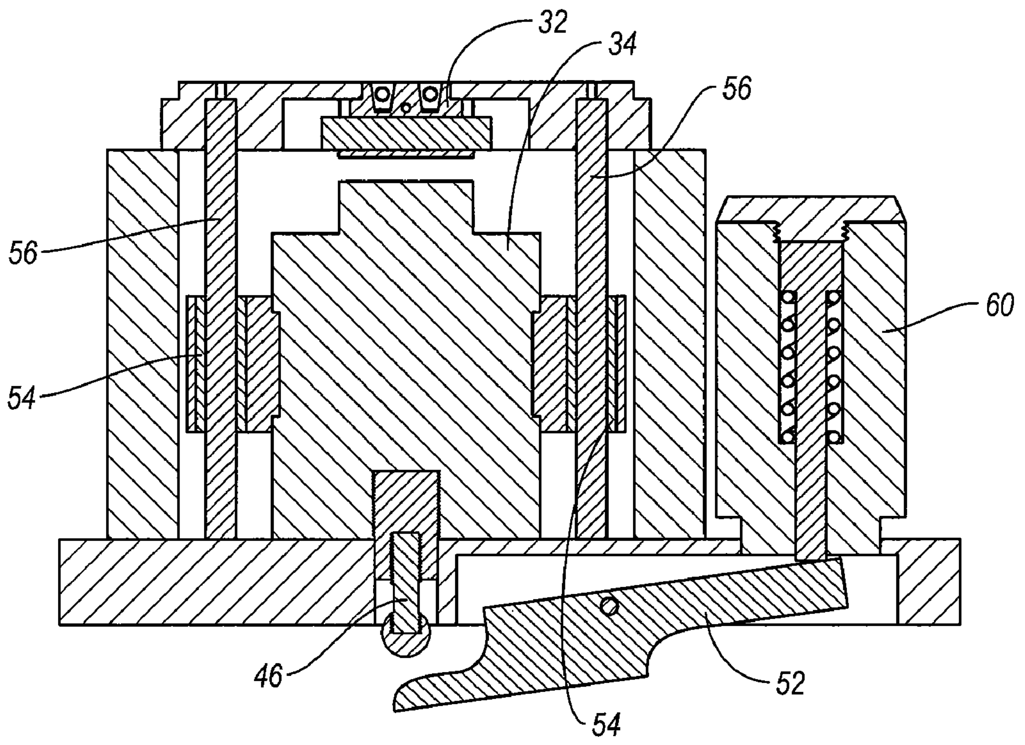
FIG. 4A is a cross-section of the embodiment of FIG. 2 shown in a position in which the sample module is thermally isolated from a cold sink.
Figure 4B:
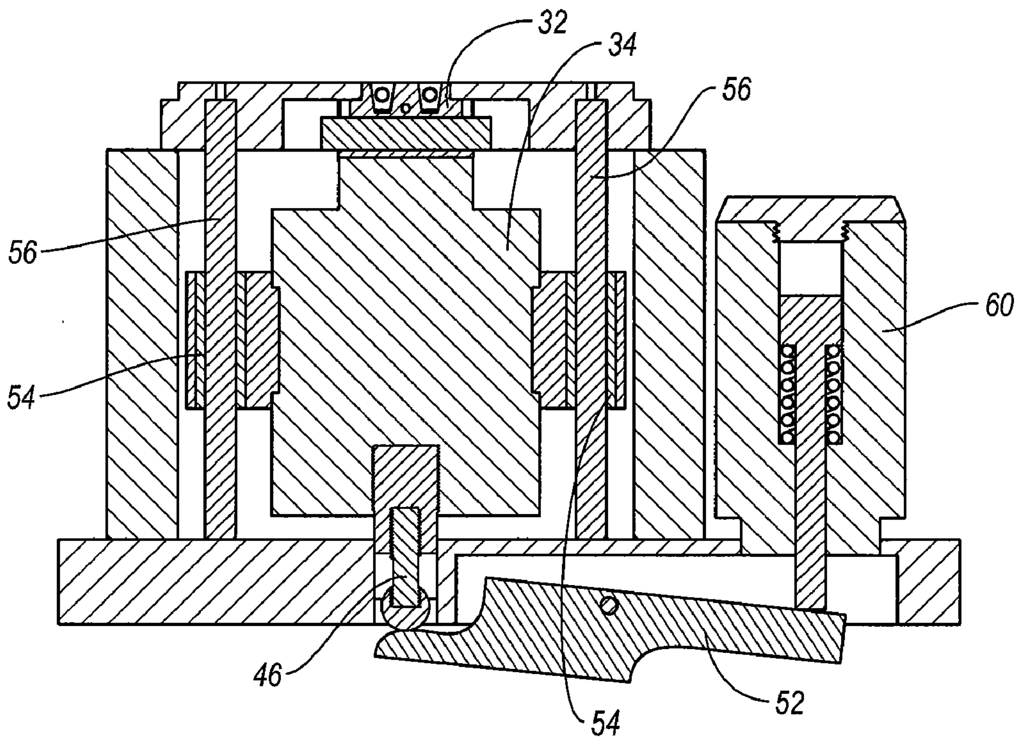
FIG. 4B is a cross-section similar to FIG. 4A, in which the sample module is in thermal communication with a cold sink.

When it is desired to bring the cold sink into contact with the sample module, a solenoid 60 is activated (See FIGS. 4A and 4B) so as to pivot lever arm 52 and to thereby raise the cold sink so that the upper surface 62 of the cold sink is in intimate contact with the under surface of sample module 32, thereby effecting cooling of the sample module. When cooling is complete, the solenoid is deactivated, allowing gravity to drop the cold sink back to a position physically isolated from the sample module. Sample module 32 is secured to top plate 64, which in FIGS. 2 and 3 is shown as having an opening 66 which exposes the top of the sample module for introducing and removing two sample vials (not shown).

Figure 5A:
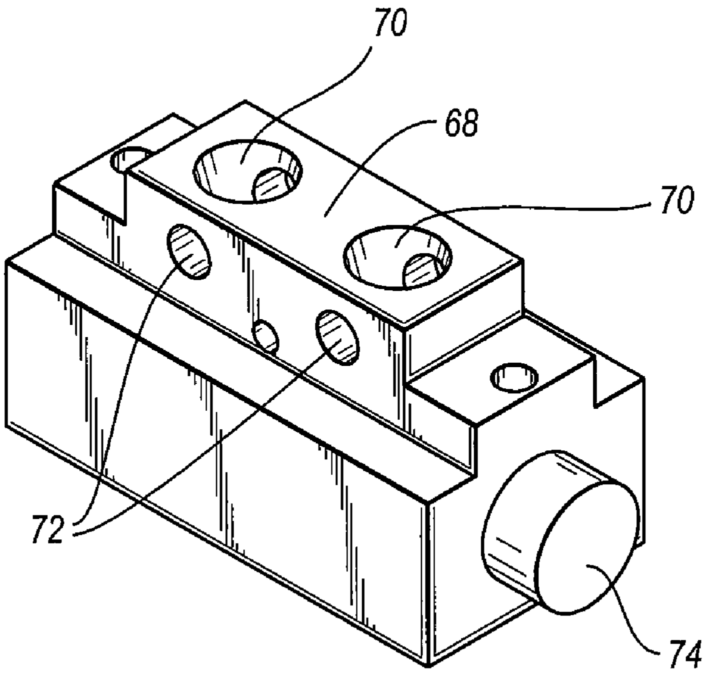
FIG. 5A is a perspective view of the sample module of FIGS. 2-4.
Figure 5B:
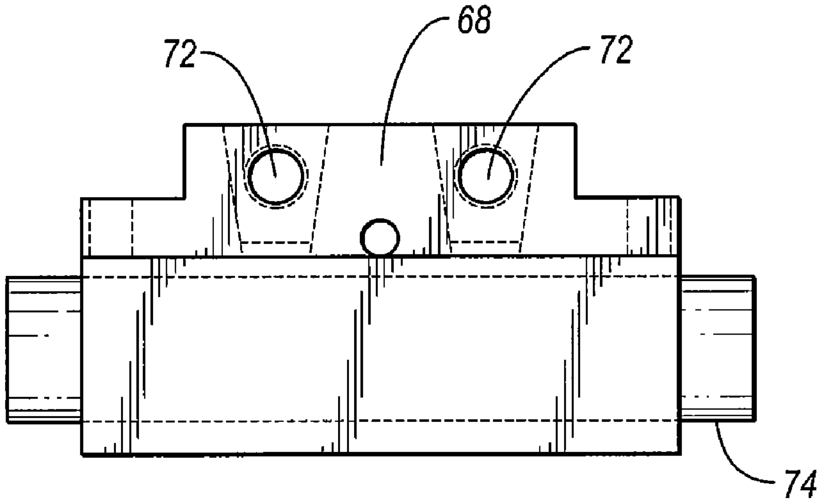
FIG. 5B is a side view of the sample module of FIG. 5A.

FIGS. 5A-5B illustrate sample module 32 in greater detail. FIG. 5A is a perspective view of the sample module, and FIG. 5B is a side view. Sample module 32 is formed from a sample block 68, which is preferably kept as small as is practical, bearing in mind that it must be large enough to hold the number of desired sample vials. Sample module 32 is preferably fabricated from any material that has a high heat transfer rate and a high heat storage capacity. As with the cold sink, one appropriate material is copper. It is preferred that a thermocouple (not shown) be provided to monitor the temperature of the sample module and that the thermocouple provide real-time information to the controller.

The sample module of FIG. 5 is provided with two wells 70, each of which is adapted to receive a sample vial (not shown). Although the illustrated embodiment provides wells which are adapted to receive a disposable vial, it should be appreciated that it is not necessary to use a disposable vial. It is also possible to utilize other geometric configurations in place of that of wells 70.

Holes 72 are optionally provided in sample module 32 for the use of sensors for monitoring the status of PCR. A bore through the sample module of the illustrated embodiment is fitted with a heating element 74. The relative thermal mass of sample block 68 and that of heating element 74 are preferably selected so as to insure that the temperature of the sample block may be increased rapidly upon activation of the heating element. This structure is an example of a sample block that can rapidly bring samples contained in sample vials that are inserted into wells 70 to a desired target temperature during the PCR cycle. Of course, other structures will be apparent in view of the teachings herein, and the heating element may merely be placed in contact with the sample module when it is necessary to raise or maintain the temperature, rather than being situated within a bore in the sample module.

In use, the PCR cycling process begins by placing sample vials with appropriate PCR chemistry in sample wells 70. The thermocycler is then activated under the operation of a programmed computer. The cold sink remains physically separated from the sample module during the denaturization step of the PCR thermal cycle. The computer activates heating element 74 in order to heat the sample assembly to the desired target temperature for the denaturation PCR step. The computer monitors a thermocouple or other temperature sensing device and controls the temperature of the sample module so as to raise and then maintain the temperature at the desired target temperature. Predetermined constants are preferably used by the computer program to adjust the temperature of sample module 32 so that the temperature inside the sample vials are appropriate for each step of the PCR process.

When the PCR protocol calls for the temperature of the PCR chemistry to drop for the annealing stage of the PCR cycle, the heating element is turned off and the solenoid 60 is activated so as to place cold sink 34 into physical contact with the sample module 32. Because of the temperature differential and the much larger mass of cold sink 34 as compared to that of sample module 32, thermal energy is rapidly removed from the sample module. The computer again monitors the temperature of the sample module and deactivates solenoid 60 when the sample block is sufficiently cooled, thereby isolating the cold sink from the sample block.

Next, the computer activates the sample block heating element to maintain the sample block at the appropriate temperature associated with the annealing step of the PCR cycle. This process is repeated for the extension step, and then may be continued for as many PCR cycles as are desired. Although described as a three step PCR process, more or fewer steps may be used. For example, it is possible to perform PCR with a two-step process, a higher temperature for denaturization (for example, 95 degrees C.), and a lower temperature for both annealing and extension (for example, 60 degrees C.). A two step process is preferred for rapid PCR.

A thermocycler in accordance with the present invention may be scaled up or down in size, features, and complexity and in a wide variety of form factors that are optimized in view of any desired number of samples, portability requirements, desirability of the sophistication of control by a controller, the type of PCR detection assembly which might be used, and other features that will be apparent to one of ordinary skill in view of the teachings herein. The illustrated embodiment of FIGS. 2-5 is easily provided in a portable package that has a low power consumption capable of being satisfied through the use of battery power.

It will be appreciated that the drawings used to describe various aspects of exemplary embodiments of the invention are diagrammatic and schematic representations of such exemplary embodiments, and are not limiting of the present invention, nor are they necessarily drawn to scale. Furthermore, specific details set forth in the foregoing description have been given in order to provide a thorough understanding of the present invention, but it will be apparent to one skilled in the art that the present invention may be practiced without these specific details or with different details. In many respects, well-known aspects of thermocyclers and of PCR have not been described in particular detail in order to avoid unnecessarily obscuring the present invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A thermocycler for use in connection with the amplification of DNA, said thermocycler comprising:

a sample module configured for holding at least one sample, said sample module having a first thermal mass;

a heating element positioned to supply heat to said sample module;

a cooling assembly configured to receive heat from said sample module and transmit heat to exterior said cooling assembly, said cooling assembly being movable between a first position wherein it is in thermal contact with said sample module to receive heat therefrom and a second position wherein it is spaced from said sample module, said cooling assembly having a second thermal mass larger than said first thermal mass and said cooling assembly having removing means operable to remove heat from said second thermal mass;

a mechanism for moving said cooling assembly between said first position and said second position; and a controller connected to said heating element, said cooling assembly and said mechanism, said controller being configured to operate said heating element between an on position in which said heating element supplies heat to said sample module and an off position in which it does not supply heat, said controller being configured to operate said mechanism to position said cooling assembly in said second position when said heating element is in said on position and to position said cooling assembly in said first position when said heating element is in said off position, and said controller being configured to operate said removing means to remove heat from said second thermal mass when said cooling assembly is in said second position.

2. The thermocycler of claim 1, wherein the sample module has a top with an aperture formed therein for holding said at least one sample, and wherein said sample module has a bottom for thermal contact with said cooling assembly.

3. The thermocycler of claim 1, wherein the first thermal mass is selected to change the temperature at the rate of at least 5 degrees C. per second.

4. The thermocycler of claim 1, wherein the sample module has a plurality of sample wells.

5. The thermocycler of claim 1, wherein the sample module has a bore therethrough, and wherein the heating element is sized for positioning within said bore.

6. The thermocycler of claim 1, further including a housing, and wherein the sample module is mechanically associated with said housing to be held immobile relative to said housing.

7. The thermocycler of claim 2, wherein the cooling assembly includes a cold sink having at least one side and a top surface positioned for contact with said bottom of said sample module and sized to effect heat transfer therebetween, and wherein said removing means includes at least one thermoelectric cooling device in contact with said at least one side of said cold sink.

8. The thermocycler of claim 1, further comprising a PCR detection assembly which monitors the status of PCR during operation.

9. The thermocycler of claim 8, wherein the controller controls the cycling of the temperature of the sample holder in response to the monitoring of the status of PCR during operation.

10. The thermocycler of claim 1, further comprising a battery connected to said heating element, to said controller and to said cooling assembly.

11. The thermocycler of claim 7 wherein said cooling assembly includes a heat sink for removing heat from said thermoelectric cooling device.

12. The thermocycler of claim 11 wherein said cooling assembly includes a fan to urge air past said heat sink.

13. The thermocycler of claim 7 wherein said cold sink has two sides and where each side of said two sides has a thermoelectric cooling device in contact therewith, and wherein a heat sink is positioned proximate each of said thermoelectric cooling devices for removing heat therefrom.

14. The thermocycler of claim 1 wherein said cooling assembly has a bottom, and wherein said mechanism includes a solenoid and a lever, said mechanism includes a lever positioned to urge said cooling assembly from said second position toward said first position.

15. The thermocycler of claim 12 wherein said thermoelectric cooling device is secured to said side of said cold sink by a thermoconductive material.

16. A thermocycler for effecting a polymerase chain reaction (PCR) said thermocycler comprising:

a sample module configured for holding at least one sample, said sample module having a first thermal mass;

a heating element positioned to supply heat to said sample module;

a cooling assembly configured to receive heat from said sample module and transmit heat to exterior said cooling assembly, said cooling assembly being movable between a first position wherein it is in thermal contact with said sample module to receive heat therefrom and a second position wherein it is spaced from said sample module, said cooling assembly having a second thermal mass larger than said first thermal mass and said cooling assembly having removing means operable to remove heat from said second thermal mass;

a mechanism for moving said cooling assembly between said first position and said second position; and a controller including a set of instructions to perform each step of said polymerase chain reaction ("PCR") and connected to operate said heating element, said mechanism and said cooling assembly in accordance with said set of instructions, said controller being configured to operate said heating element between an on position in which said heating element supplies heat to said sample module and an off position in which it does not supply heat, said controller being configured to operate said mechanism to position said cooling assembly in said second position when said heating element is in said on position and to position said cooling assembly in said first position when said heating element is in said off position, and said controller being configured to operate said removing means to remove heat from said second thermal mass when said cooling assembly is in said second position.

* * * * *